(12) United States Patent
Mahani et al.

(10) Patent No.: US 10,295,680 B2
(45) Date of Patent: May 21, 2019

(54) POSITRON RANGE REDUCTION IN POSITRON EMISSION TOMOGRAPHY IMAGING

(71) Applicants: Hojjat Mahani, Esfahan (IR); Mustafa Abbasi, Shiraz (IR); Mohammad Reza Ay, Tehran (IR); Saeed Sarkar, Tehran (IR); Mohammad Hossein Farahani, Tehran (IR)

(72) Inventors: Hojjat Mahani, Esfahan (IR); Mustafa Abbasi, Shiraz (IR); Mohammad Reza Ay, Tehran (IR); Saeed Sarkar, Tehran (IR); Mohammad Hossein Farahani, Tehran (IR)

(73) Assignee: PARTO NEGAR PERSIA CO., Tehran (IR)

( * ) Notice: Subject to any disclaimer, the term of this patent is extended or adjusted under 35 U.S.C. 154(b) by 0 days.

(21) Appl. No.: 15/847,809

(22) Filed: Dec. 19, 2017

(65) Prior Publication Data
US 2018/0113225 A1    Apr. 26, 2018

Related U.S. Application Data

(60) Provisional application No. 62/435,877, filed on Dec. 19, 2016.

(51) Int. Cl.
*G01T 1/29* (2006.01)
*A61B 6/03* (2006.01)

(52) U.S. Cl.
CPC ............ *G01T 1/2985* (2013.01); *A61B 6/037* (2013.01)

(58) Field of Classification Search
CPC .............................. A61B 6/037; G01T 1/2985
See application file for complete search history.

(56) References Cited

U.S. PATENT DOCUMENTS

| 4,939,464 A | 7/1990 | Hammer | |
| 5,055,789 A * | 10/1991 | Kondo | G01R 33/56554 324/309 |
| 7,759,647 B2 | 7/2010 | Grazioso | |
| 2014/0228673 A1 * | 8/2014 | Watson | A61B 6/5247 600/411 |

OTHER PUBLICATIONS

Huang et al. "The effect of magnetic field on positron range and spatial resolution in an integrated whole-body time-of-flight PET/MRI system." Nuclear Science Symposium and Medical Imaging Conference (NSS/MIC), 2014 IEEE. IEEE, 2014, pp. 1-4.

(Continued)

*Primary Examiner* — Marcus H Taningco
(74) *Attorney, Agent, or Firm* — NovoTechIP International PLLC

(57) ABSTRACT

Methods and systems are disclosed, including a method for confining an annihilation range of a positron, from a plurality of positrons emitted from an object being imaged in a positron emission tomography (PET) imaging system. Confining the annihilation includes applying a stochastic multidimensional time varying magnetic field on the positron. Optionally, the stochastic multidimensional time varying magnetic field includes components in each of three dimensions.

17 Claims, 6 Drawing Sheets

(56) References Cited

OTHER PUBLICATIONS

Peng et al. "Study of PET intrinsic spatial resolution and contrast recovery improvement for PET/MRI systems." Physics in medicine and biology, 2012, vol. 57, No. 9, pp. N101-N115.

Herzog et al. "Influence from high and ultra-high magnetic field on positron range measured with a 9.4 TMR-BrainPET." Nuclear Science Symposium Conference Record (NSS/MIC), 2010 IEEE. IEEE, 2010, pp. 3410-3413.

Shah et al. "Effects of magnetic fields of up to 9.4 T on resolution and contrast of PET images as measured with an MR-BrainPET." PloS one, 2014, vol. 9, No. 4, p. e95250.

Wirrwar et al. "4.5 tesla magnetic field reduces range of high-energy positrons-potential implications for positron emission tomography." IEEE Transactions on Nuclear Science, 1997, vol. 44, No. 2, pp. 184-189.

Bertolli et al. "PET iterative reconstruction incorporating an efficient positron range correction method." Physica Medica, 2016, vol. 32, No. 2, pp. 323-330.

Burdette et al. "Very high resolution small animal PET in strong magnetic fields." Nuclear Science Symposium Conference Record, 2006. IEEE. IEEE, 2006, vol. 4, pp. 2417-2420.

Cherry et al. "The integration of positron emission tomography with magnetic resonance imaging." Proceedings of the IEEE, 2008, vol. 96, No. 3, pp. 416-438.

Christensen et al. "Positron emission tomography within a magnetic field using photomultiplier tubes and lightguides." Physics in medicine and biology, 1995, vol. 40, No. 4, pp. 691-697.

Albani. "Constrained Positron Flight in PET Imaging via Strong Magnetic Fields." Diss. The Ohio State University, 2008.

Hammer et al. "Use of a magnetic field to increase the spatial resolution of positron emission tomography." Medical physics, 1994, vol. 21, No. 12, pp. 1917-1920.

Iida et al. "A simulation study of a method to reduce positron annihilation spread distributions using a strong magnetic field in positron emission tomography." IEEE Transactions on Nuclear Science, 1986, vol. 33, No. 1, pp. 597-600.

Mashayekhi et al. "Calculation of Positron Distribution in the Presence of a Uniform Magnetic Field for the Improvement of Positron Emission Tomography (PET) Imaging Using GEANT4 Toolkit." Iranian Journal of Medical Physics, 2015, vol. 12, No. 1, pp. 7-13.

Burdette. "A study of the effects of strong magnetic fields on the image resolution of PET scanners." The Ohio State University, 2009.

Raylman et al. "Combined MRI-PET scanner: a Monte Carlo evaluation of the improvements in PET resolution due to the effects of a static homogeneous magnetic field." IEEE Transactions on Nuclear Science, 1996, vol. 43, No. 4, pp. 2406-2412.

* cited by examiner

POSITRON RANGE REDUCTION IN POSITRON EMISSION TOMOGRAPHY IMAGING

CROSS-REFERENCE TO RELATED APPLICATION

This application claims the benefit of priority from U.S. Provisional Patent Application Ser. No. 62/435,877, filed on Dec. 19, 2016, and entitled "REDUCTION OF POSITRON RANGE IN HIGH-RESOLUTION PET IMAGING," which is incorporated herein by reference in its entirety.

SPONSORSHIP STATEMENT

This application has been sponsored by Iran Patent Center, which does not have any rights in this application.

TECHNICAL FIELD

The present disclosure generally relates to positron emission tomography, and particularly, to positron confinement in positron emission tomography imaging.

BACKGROUND

Positron Annihilation Lifetime Spectroscopy (PALS) is a technique for direct measurement of sub-nanometer sized molecular free volumes. General operations in the PALS technique includes emitting positrons from an inspection region in a material being tested and then measuring the length of time until it annihilates with one of the material's electrons, producing gamma rays Positrons are antiparticles of electrons. A positron collision with an electron results in the annihilation of both particles and an emission of two characteristic 511 keV gamma rays. The lifetime of positrons is a measure of the local electron density at the point of annihilation. The annihilation can be detected by virtue of the gamma rays emitted. Positron lifetime techniques are among the few methods that are sensitive to voids on the mono-atomic scale.

Spatial resolution of the PET tomograms is limited by positron range. Traveling of the positrons in human tissue before undergoing annihilation may lead to a positional inaccuracy, which reduce a PET image quality. One technique directed to the positron range issue applies a static axial magnetic field on the positrons. When positrons are in the axial magnetic field, they experience a Lorentz force. Since the Lorentz force is perpendicular to the applied magnetic field direction, the positrons may freely fly along the magnetic field direction while being constrained in all planes whose normal vector is in the applied magnetic field direction.

One shortcoming of the axial magnetic field technique is that the positron range may be confined only in the transaxial plane, i.e., plane(s) transverse to the direction of the magnetic field. Costs of the axial magnetic field technique therefore include a loss in the axial resolution (along the magnetic field direction). The loss of axial resolution can produce a shine-through artifact, which degrades image quality. One additional shortcoming of the axial magnetic field technique is that a high strength (up to 10 T) is required for the applied magnetic field to effectively confine the positron range in the transaxial plane.

There is, therefore, a need in the art for a method to confine the annihilation rage of positrons in all three dimensions in PET imaging systems. There is also a need in the art for a confining of the positron annihilation range, without requiring high-strength magnetic fields.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

One general aspect of the disclosure provides a method for confining an annihilation range of a positron from a plurality of positrons emitted from an object being imaged in a positron emission tomography (PET) imaging system. In one particular aspect thereof, the method can include applying a stochastic magnetic field on the positron. Technical features of systems and methods according to the present disclosure include confinement of positrons, and hence the range of their annihilation. Another technical feature includes imaging processes requiring significantly lower magnitude magnetic fields than those required by the axial magnetic field technique, among other features and advantages. These features can, in turn, provide significant increase of the PET image resolution.

Specific features of the above described general aspect can include one or more of the following features. In some implementations, applying the stochastic magnetic field can include applying a time-varying magnetic field. In other implementations, applying the stochastic magnetic field may include applying a periodic magnetic field. In some examples, applying the stochastic magnetic field can include applying a multidimensional magnetic field. In some implementations, the stochastic magnetic field can be configured, in part, by a stochastic process. One example stochastic process can have a uniform probability distribution. In an implementation, frequency of the stochastic magnetic field can be significantly larger than the positron annihilation rate. In an aspect, the frequency of the stochastic magnetic field can be significantly larger than the positron thermalization rate. In an example, an amplitude and frequency of the stochastic magnetic field can be configured such that a relativistic positron gyro radius and a maximum free flight traveled by the positron become significantly smaller than a transport length of the positron. In one or more implementations, an angular frequency of the stochastic magnetic field can be significantly larger than a relativistic gyro frequency of the positron.

One general aspect of the disclosure includes a system for confining an annihilation range of a positron from a plurality of positrons emitted from an object being imaged by a PET imaging system can include a magnetic field supplier, configured to apply a stochastic time-varying multidimensional magnetic field on the positron.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary implementations of the present disclosure. For purposes of explanation, for providing a thorough understanding of the present disclosure, specific examples and details thereof are set forth. Upon reading this disclosure it will become apparent to one skilled in the art that these specific details are not required to practice the disclosed aspects. Descriptions of specific exemplary implementations are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The present disclosure describes implementations of a method and a system that provides increase in the image resolution in PET imaging. Features of the method and system include confining the annihilation range of positrons emitted from a patient being imaged. In an aspect, a stochastic and time-varying magnetic field can be applied on the positrons, the field having aspects that can provide annihilation of each emitted positron before it travels a limited distance from its creation point in every dimension. In other words, each positron can be confined to a small sphere centered at the positron creation point. That confinement, in turn, can enhance the detection of positron creation points. Enhancing the detection of positron creation points can improve the spatial resolution of images.

Exemplary methods and systems according to various aspects of the present disclosure can include application of a stochastic magnetic field on the positrons that are emitted from the object being imaged. In an aspect, application of a stochastic magnetic field, in particular, a controlled magnetic field to extant in a region that includes the location of positron, can effect control of a movement of such positrons. In an aspect, control of the movement, by control of the magnetic field, can provide a control of the annihilation range of positrons.

In some implementations, applying the stochastic magnetic field can include applying a time-varying magnetic field. According to various aspects, applying the time-varying magnetic field can include applying a periodic magnetic field. In some cases, applying the stochastic magnetic field can include applying a multidimensional magnetic field. Applying a multidimensional magnetic field may allow for controlling the movement of positrons in each dimension independently in a three-dimensional space.

Figure 1:
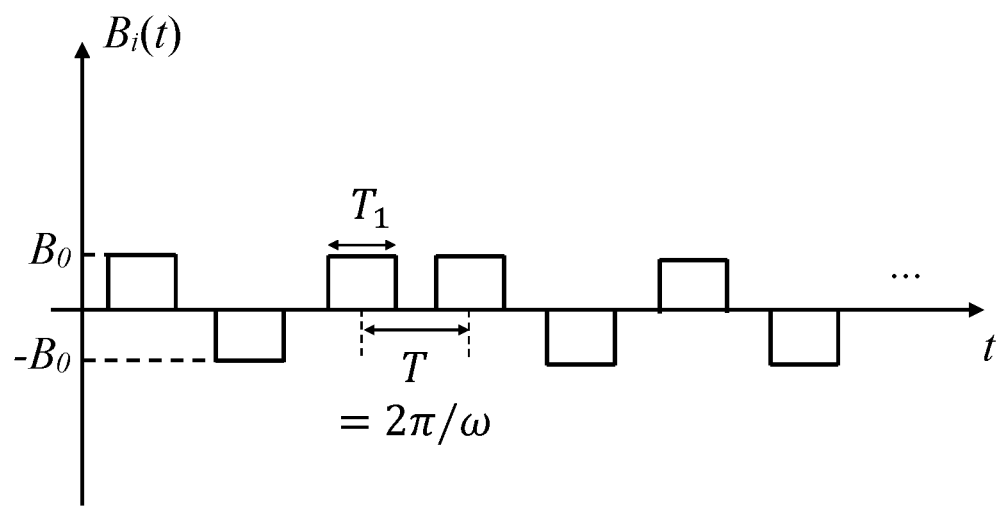
FIG. 1 is a diagram illustrating variations of an exemplary stochastic magnetic field versus time.

FIG. 1 illustrates a diagram of an exemplary stochastic magnetic field versus time, of a stochastic magnetic field according to the present disclosure. In some implementations, applying the stochastic magnetic field can include configuring the stochastic magnetic field according to Equation 1 below:

$$B_i(t) = B_0 \sum_{n=0}^{\infty} \text{sgn}(N_i(nT)) \text{rect}\left(\frac{t - nT}{T_1}\right) \qquad \text{Equation (1)}$$

where
i=1, 2, 3 is a spatial component of the stochastic magnetic field,
t is a time instant,
$B_0$ is an overall amplitude of the stochastic magnetic field in the spatial component i,
sgn is a sign function,
$N_i(t)$ is a stochastic process defined in the spatial component i,
rect is a rectangular function,
$T_1$ is a width of the rectangular function, and
$T=2\pi/\omega$ is a period of the stochastic magnetic field, with $\omega$ being an angular frequency of the stochastic magnetic field.

In some implementations, the stochastic process $N_i(t)$ can have a uniform probability distribution with a range of [−½, ½], and the width of the rectangular function $T_1$ can equal half of the period T.

In some implementations, the angular frequency of the stochastic magnetic field can satisfy the following condition:

$\omega \gg 2\pi\lambda$, where $\lambda$ is the positron annihilation rate.

In other words, according to one aspect, the angular frequency of the stochastic magnetic field can be significantly larger than the frequency of positron annihilation. Application of a stochastic magnetic field according to this aspect can provide, among features, the positron being annihilated in a much smaller range than the natural annihilation range of the positron (determined by $\lambda$).

In other implementations, the angular frequency of the stochastic magnetic field can satisfy the following condition:

$\omega \gg 2\pi/\tau_{thermalization}$, where $\tau_{thermalization}$ is thermalization time of the positron. In other words, the angular frequency of the stochastic magnetic field can be selected significantly larger than the frequency of positron thermalization. Applying the stochastic magnetic field according to this aspect can cause the positron to be annihilated in a much smaller range than the natural thermalization range of the positron (determined by $\tau_{thermalization}$).

Identifying the proper and effective amplitude and the angular frequency of the stochastic magnetic field can be performed using operations that include modelling a movement of the positrons, by a random walk process. In an aspect, associated with a random walk process, x can represent the distance traveled by a random walker after N steps with $l_k$ representing the displacement at the $k^{th}$ step. In one implementation according to this aspect, example random walk process x can be according to the following Equation (2):

$$x = l_1 + l_2 + l_3 + \ldots + l_N = \sum_{k=1}^{N} l_k \qquad \text{Equation (2)}$$

The average value $\langle x \rangle$ of x for a plurality of independent random walkers can be given by the following Equation (3)

$$\langle x \rangle = \langle \sum_{k=1}^{N} l_k \rangle = \sum_{k=1}^{N} \langle l_k \rangle = 0 \qquad \text{Equation (3)}$$

By modelling the positron as a random walker, the displacement $l_k$ at each dimension can be estimated, for example, according to the following Equation (4)

$$l_k \square l_{initial} + \frac{\omega_c}{\omega} R_L = v_{initial} \frac{2\pi}{\omega} + \frac{\omega_c}{\omega} R_L \qquad \text{Equation (4)}$$

where
- $v_{initial}$ is the initial velocity of emitted positions in a random direction,
- $R_L$ is a relativistic positron gyro radius for each space component, and
- $l_{initial}$ is a maximum free flight traveled by the positron, where "maximum free flight" means a distance reached by the positron within a time interval corresponding to half of the period of the stochastic magnetic field with the initial speed $v_{initial}$.

According to Equation 4, the equality in Equation 3 can be satisfied if $v_{initial}$ $$\frac{2\pi}{\omega}$$

and $R_L$ can be estimated as zero. That condition for satisfaction can be approximately satisfied if $v_{initial}$ $$\frac{2\pi}{\omega}$$

and $R_L$ are negligible with respect to the transport length of the positron.

In other implementations, the angular frequency of the stochastic magnetic field can satisfy the following condition:

$$\omega >> 2\pi/\tau_{thermalization},$$

where
$\tau_{thermalization}$ is thermalization time of the positron.

In other words, the angular frequency of the stochastic magnetic field can be configured significantly larger than the frequency of positron thermalization, so that applying the stochastic magnetic field may cause the positron to be annihilated in a much smaller range than the natural thermalization range of the positron (determined by $\tau_{thermalization}$).

In some implementations, the amplitude and the angular frequency of the stochastic magnetic field can be configured such that the following conditions are satisfied:

$$\frac{\omega_c}{\omega} R_L << L_T \text{ and } v_{initial} \frac{2\pi}{\omega} << L_T$$

where
$L_T$ is a transport length of the positron,
$v_{initial}$ is an initial velocity of the positron, and
$R_L$ is a relativistic positron gyro radius.

The relativistic gyro position radius, $R_L$, can be according to the following Equation (5), $$R_L = \frac{1}{\omega_c} \left( 1 - \frac{m_{positron}^2 C^4}{(E + m_{positron} C^2)^2} \right)^{1/2} C \qquad \text{Equation (5)}$$

where
- $m_{positron}$ is mass of the positron,
- C is the speed of light,
- E is the kinetic energy of the plurality of positrons, and
- $\omega_c$ is a relativistic gyro frequency.

The relativistic gyro frequency, $\omega_c$, can be according to the following Equation (6):

$$\omega_c = \frac{eB_0}{\gamma m_{positron}} \qquad \text{Equation (6)}$$

where
- e is the elementary charge,
- $B_0$ is the amplitude of the stochastic magnetic field, and
- $\gamma$ is the Lorentz factor.

In some implementations, the angular frequency of the stochastic magnetic field can be configured to satisfy the following condition:

$$\omega >>> \omega_c.$$

Figure 2:
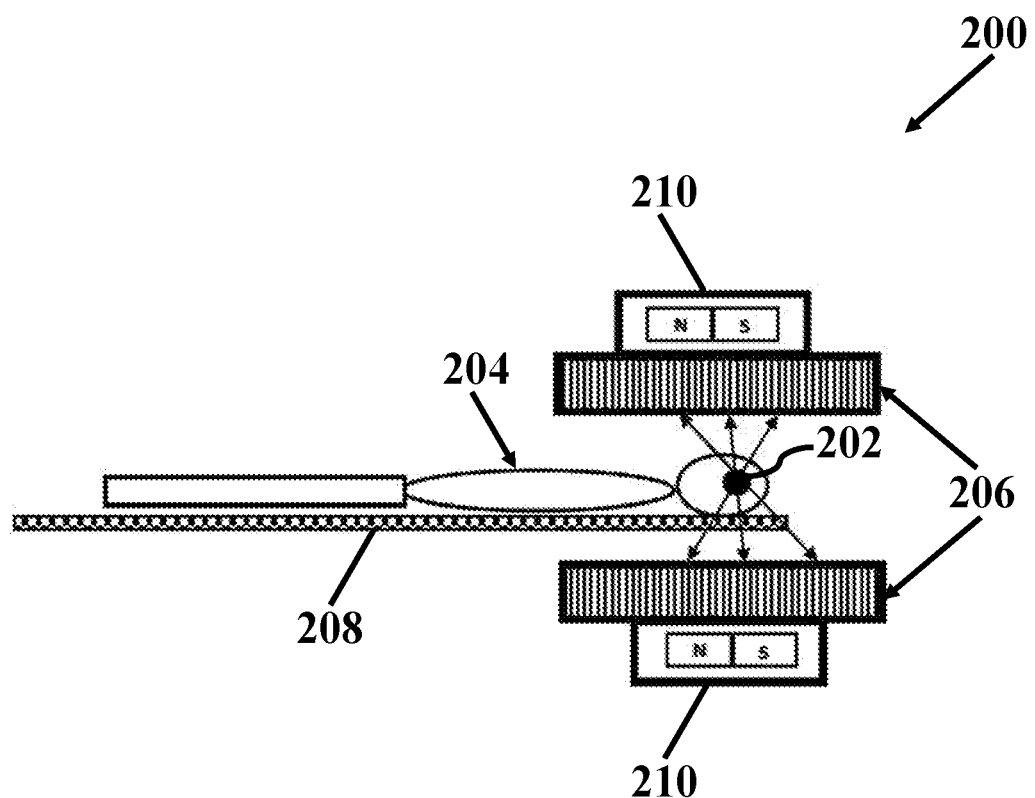
FIG. 2 illustrates an implementation of a system for confining an annihilation range of a positron.

FIG. 2 illustrates an implementation of a system 200 for confining an annihilation range of a positron from a plurality of positrons 202, according to one example implementation of the present disclosure. The plurality of positrons 202 may be emitted from an object 204 being imaged by a PET imaging system 206. In an implementation, the object 204 can be a patient laid on a couch 208 and the system 200 may further include a magnetic field supplier 210. The magnetic field supplier 210 can be configured to apply the stochastic magnetic field defined by Equation 1 on the plurality of positrons 202.

Figure 3:
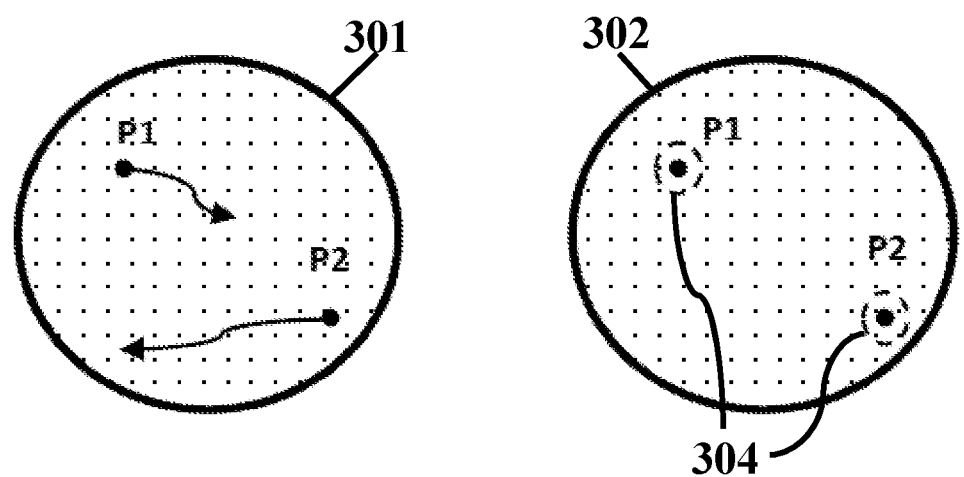
FIG. 3 illustrates a schematic of positron confinement according to a bulk confining method from the prior art (left) and the present disclosure (right).

FIG. 3 illustrates a schematic of positron confinement according to a bulk confining method from the prior art (left) and an implementation of the method disclosed herein (right). Referring to FIG. 3, two exemplary positrons P1 and P2 from a plurality of positrons are depicted. The plurality of positrons may be confined in a left bulk 301 by using the bulk confining method. Each of the plurality of positrons may move to any point inside the left bulk 301, as shown in the left bulk 301 in FIG. 3. However, utilizing an implementation of the method disclosed herein may allow for confining each of the plurality of positrons, for example P1 and P2 inside spheres 304 with a radius proportional to the relativistic positron gyro radius $R_L$, as shown in the right bulk 302

Example: Positron Confinement by Applying a Magnetic Field

Figure 4A:
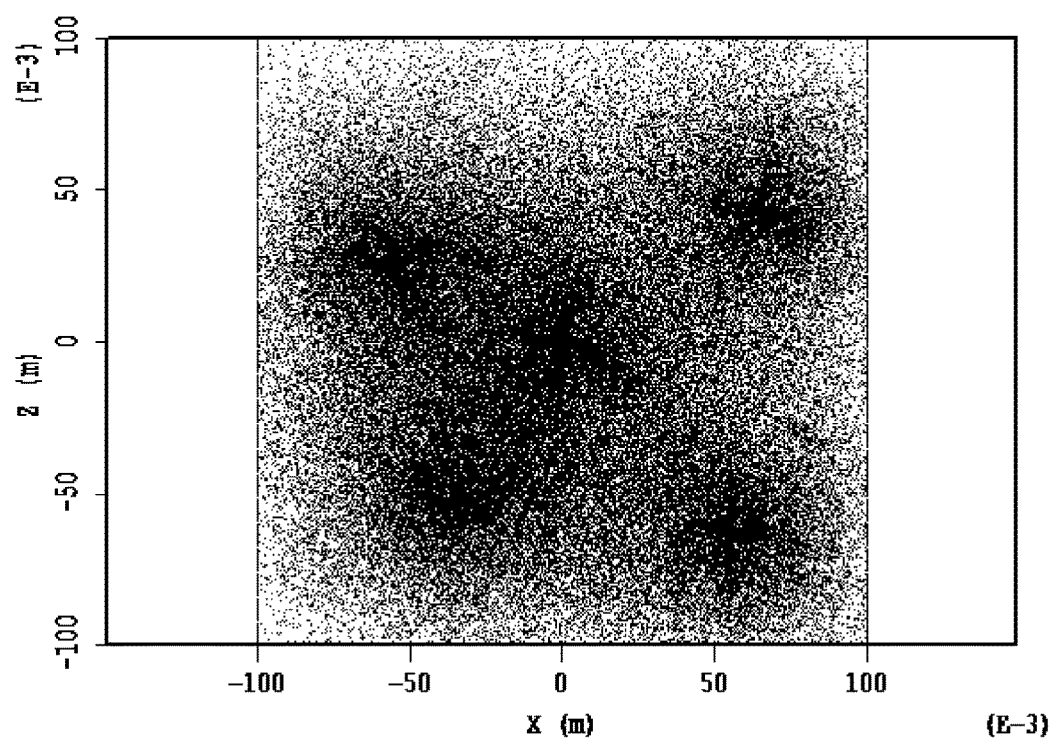
FIG. 4A illustrates a two-dimensional cross-section of location distribution for five exemplary simulated positrons emitted in a 20 cm×20 cm×20 cm vacuum, according to one implementation of the present disclosure.

FIG. 4A illustrates a two-dimensional cross-section of location distribution for five exemplary simulated positrons emitted in a 20 cm×20 cm×20 cm vacuum. No magnetic field is applied on the exemplary simulated positrons. It can be observed in FIG. 4A that the positrons may scatter in almost the entire vacuum. In other words, the annihilation range of the positrons is not confined.

Figure 4B:
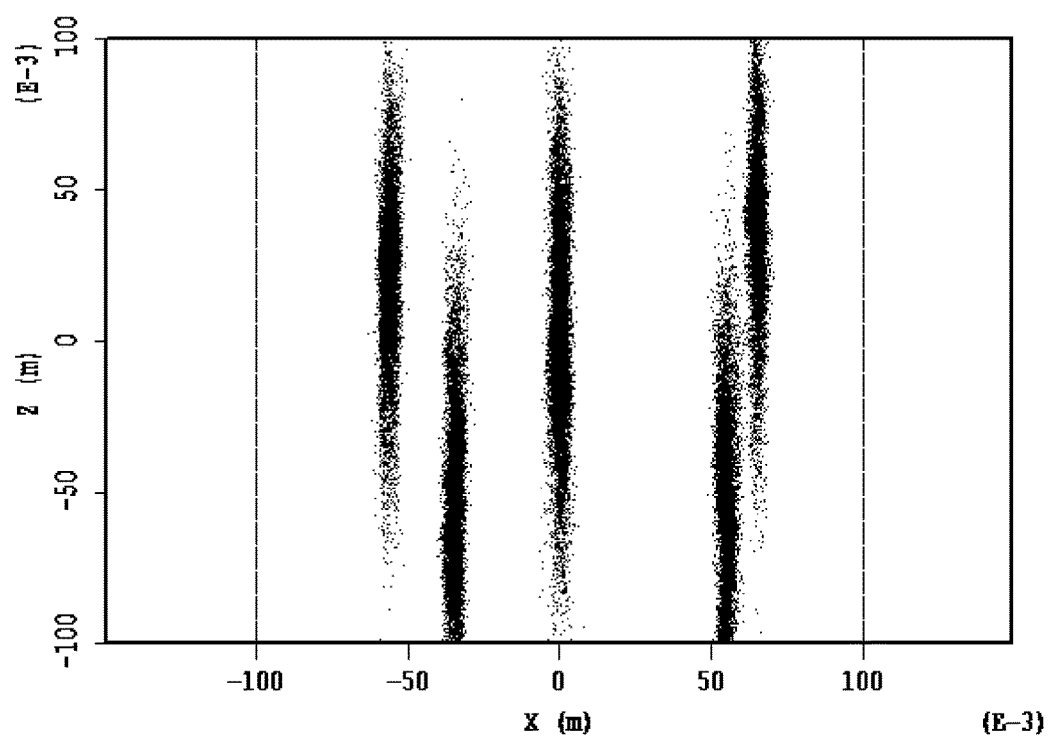
FIG. 4B illustrates a location distribution for simulated positrons when a permanent magnetic field is applied on the positrons along the z-axis.

FIG. 4B illustrates the location distribution for the simulated positrons when a permanent magnetic field is applied on the positrons along the z-axis, according to a prior art. It can be seen that the positrons are confined in two dimensions but may scatter along the z-axis. Thus, the annihilation range of the positrons is not confined in three dimensions.

Figure 4C:
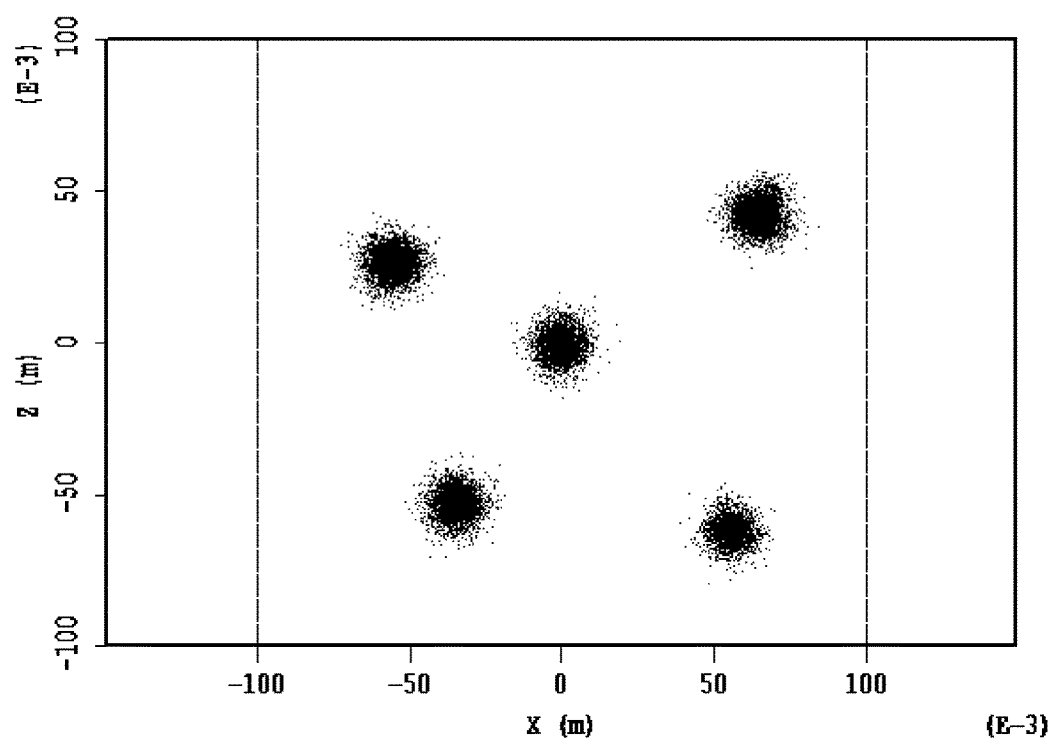
FIG. 4C illustrates a location distribution for simulated positrons when a stochastic magnetic field is applied on the positrons, according to an implementation of the present disclosure.

FIG. 4C illustrates the location distribution for the simulated positrons when a stochastic magnetic field, as defined in equation 1, is applied on the positrons, according to an implementation of the method disclosed herein. The amplitude of the stochastic magnetic field was set to $B_0$=5 T and the frequency of the stochastic magnetic field was set to $\omega/2\pi$=600 GHz. These values fulfill the amplitude and frequency conditions of the stochastic magnetic field for confining the positron annihilation range, and are also accessible by current common technologies. It can be seen in FIG. 4C that the positrons are confined in all three dimension. Each of the positrons is confined inside a sphere with a radius proportional to the relativistic positron gyro radius $R_L$.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for confining an annihilation range of a positron from a plurality of positrons emitted from an object being imaged in a positron emission tomography (PET) imaging system, the method comprising applying a stochastic time-varying multidimensional magnetic field on the positron, wherein the stochastic time-varying multidimensional magnetic field is according to the following:

$$B_i(t) = B_0 \sum_{n=0}^{\infty} \text{sgn}(N_i(nT)) rect\left(\frac{t-nT}{T_1}\right),$$

where i=1, 2, 3 is a spatial component of the stochastic time-varying multidimensional magnetic field;
t is a time instant;
$B_0$ is an amplitude of the stochastic time-varying multidimensional magnetic field in the spatial component;
sgn is a sign function;
$N_i(t)$ is a stochastic process with a uniform distribution with a range of $[-\frac{1}{2}, \frac{1}{2}]$ in the spatial component i;
rect is a rectangular function;
$T=2\pi/\omega$ is a time period of the stochastic time-varying multidimensional magnetic field, where ω is an angular frequency of the stochastic time-varying multidimensional magnetic field; and
$T_1=T/2$ is a width of the rectangular function, wherein the angular frequency and the amplitude of the stochastic time-varying multidimensional magnetic field are configured such that the following conditions are satisfied:

$\omega \gg 2\pi\lambda$ and $\omega \gg 2\pi/\tau_{thermalization}$ and $\omega \ggg \omega_c$ and $$\frac{\omega_c}{\omega} R_L \ll L_T \text{ and } v_{initial} \frac{2\pi}{\omega} \ll L_T,$$

where $\lambda$ is an annihilation rate of the positron;
$\tau_{thermalization}$ is a thermalization time of the positron;
$L_T$ is a transport length of the positron;
$v_{initial}$ is an initial velocity of the positron; and
$R_L$ is a relativistic positron gyro radius defined by the following:

$$R_L = \frac{1}{\omega_c}\left(1 - \frac{m_{positron}^2 C^4}{(E + m_{positron}C^2)^2}\right)^{1/2} C,$$

where $m_{positron}$ is mass of the positron;
C is the speed of light;
E is the kinetic energy of the plurality of positrons; and
$\omega_c$ is a relativistic gyro frequency according to the following:

$$\omega_c = \frac{eB_0}{\gamma m_{positron}},$$

where e is the elementary charge and $\gamma$ is the Lorentz factor.

2. A method for confining an annihilation range of a positron from a plurality of positrons emitted from an object being imaged in a positron emission tomography (PET) imaging system, the method comprising applying a stochastic magnetic field on the positron,
wherein applying the stochastic-magnetic field includes applying a time-varying magnetic field.

3. The method of claim 2, wherein applying the time-varying magnetic field includes applying a periodic magnetic field.

4. The method of claim 2, wherein applying the time-varying magnetic field includes applying a multidimensional time-varying magnetic field.

5. The method of claim 2, wherein applying the time-varying magnetic field includes applying a stochastic time-varying magnetic field according to the following:

$$B_i(t) = B_0 \sum_{n=0}^{\infty} \text{sgn}(N_i(nT)) rect\left(\frac{t-nT}{T_1}\right),$$

where i=1, 2, 3 is a spatial component of the stochastic time-varying magnetic field;
t is a time instant;
$B_0$ is an amplitude of the stochastic time-varying magnetic field in the spatial component;
sgn is a sign function;
$N_i(t)$ is a stochastic process defined in the spatial component i;
rect is a rectangular function;
$T=2\pi/\omega$ is a period of the stochastic time-varying magnetic field, where $\omega$ is an angular frequency of the stochastic time-varying magnetic field; and
$T_1$ is a width of the rectangular function.

6. The method of claim 5, wherein the stochastic process $N_i(t)$ has a uniform probability distribution with a range of $[-\frac{1}{2}, \frac{1}{2}]$, and the width of the rectangular function $T_1$ equals half of the period T.

7. The method of claim 5, wherein the angular frequency of the stochastic time-varying magnetic field satisfies the following condition:

$\omega \gg 2\pi\lambda$, where $\lambda$ is the positron annihilation rate.

8. The method of claim 5, wherein the angular frequency of the stochastic time-varying magnetic field satisfies the following condition:

$\omega \gg 2\pi/\tau_{thermalization}$, where $\tau_{thermalization}$ is a thermalization time of the positron.

9. The method of claim 5, wherein the amplitude and the angular frequency of the stochastic time-varying magnetic field are such that the following conditions are satisfied:

$$\frac{\omega_c}{\omega} R_L \ll L_T \text{ and } v_{initial} \frac{2\pi}{\omega} \ll L_T,$$

where $L_T$ is a transport length of the positron;
$v_{initial}$ is an initial velocity of the positron; and
$R_L$ is a relativistic positron gyro radius defined by the following:
$R_L$=according to the following:

$$\omega_c = \frac{eB_0}{\gamma m_{positron}},$$

where
e is the elementary charge;
$B_0$ is the amplitude of the stochastic magnetic field; and
$\gamma$ is the Lorentz factor.

10. The method of claim 9, wherein the angular frequency of the stochastic time-varying magnetic field satisfies the following condition:

$\omega \ggg \omega_c$.

11. A system for confining an annihilation range of a positron from a plurality of positrons emitted from an object being imaged by positron emission tomography (PET) imaging, the system comprising a magnetic field supplier configured to apply a stochastic time-varying multidimensional magnetic field on the positron.

12. The system of claim 11, wherein the stochastic time-varying multidimensional magnetic field is according to the following:

$$B_i(t) = B_0 \sum_{n=0}^{\infty} \text{sgn}(N_i(nT)) rect\left(\frac{t-nT}{T_1}\right),$$

where i=1, 2, 3 is a spatial component of the stochastic time-varying multidimensional magnetic field;
t is a time instant; $B_0$ is an amplitude of the stochastic time-varying multidimensional magnetic field in the spatial component;
sgn is a sign function;

$N_i(t)$ is a stochastic process with a uniform distribution with a range of $[-\frac{1}{2}, \frac{1}{2}]$ in the spatial component i;

rect is a rectangular function;

$T=2\pi/\omega$ is a time period of the stochastic time-varying multidimensional magnetic field, where $\omega$ is an angular frequency of the stochastic time-varying multidimensional magnetic field; and $T_1=T/2$ is a width of the rectangular function.

13. The system of claim 12, wherein the angular frequency and the amplitude of the stochastic time-varying multidimensional magnetic field satisfy the following:

$$\omega \gg 2\pi\lambda \text{ and } \omega \gg 2\pi\tau_{thermalization} \text{ and } \omega \ggg \omega_c \text{ and}$$

$$\frac{\omega_c}{\omega} R_L \ll L_T \text{ and } v_{initial} \frac{2\pi}{\omega} \ll L_T,$$

where $\lambda$ is annihilation rate of the positron;

$\tau_{thermalization}$ is thermalization time of the positron;

$L_T$ is a transport length of the positron;

$v_{initial}$ is an initial velocity of the positron; and $R_L$ is a relativistic positron gyro radius defined by the following:

$$R_L = \frac{1}{\omega_c}\left(1 - \frac{m_{positron}^2 C^4}{(E + m_{positron}C^2)^2}\right)^{1/2} C,$$

where $m_{positron}$ is mass of the positron;

C is the speed of light;

E is the kinetic energy of the plurality of positrons; and $\omega_c$ is a relativistic gyro frequency of the positron calculated by an operation defined by the following:

$$\omega_c = \frac{eB_0}{\gamma m_{positron}},$$

where e is the elementary charge and $\gamma$ is the Lorentz factor.

14. A method for confining an annihilation range of a positron from a plurality of positrons emitted from an object being imaged in a positron emission tomography (PET) imaging system, the method comprising:

creating, at a time t, the positron at a position within the object; and over a time period extending from t, confining the annihilation range along each of three mutually orthogonal reference axes that extend from the position, wherein the controllable confining includes:

applying, for each of the three mutually orthogonal reference axes a stochastic time-varying multidimensional magnetic field, over the time period, the field having a spatial component along each of the three mutually orthogonal reference axes, each spatial component having an amplitude, wherein:

each amplitude, at t, is based at least in part on a running sum of n products, n ranging from 0 to infinity, the elements of each of the products include a sgn of a stochastic process at a time nT, corresponding to the reference axis, the elements of each of the products further include a rectangle function of an argument that includes t and nT, T is a duration that is based, at least in part, on an angular frequency of the time-varying stochastic magnetic field, the angular frequency is greater than an annihilation rate of the positron, scaled by a constant, and is greater than an inverse of a thermalization time of the positron scaled by the constant the angular frequency is much greater than a relativistic gyro frequency of the positron, a ratio of the angular frequency to the relativistic gyro frequency of the positron is greater than a ratio of a relativistic gyro radius of the positron to a transport length of the positron, and the relativistic gyro radius of the positron is based, at least in part on a combination that includes, concurrently, all among a mass of the positron, the speed of light, a relativistic gyro frequency of the positron, and a kinetic energy of the positron.

15. The method of claim 14, wherein T is based on:

$T=2\pi/\omega$, and is a time period of the stochastic time-varying multidimensional magnetic field, where $\omega$ is the angular frequency.

16. The method of claim 14, wherein the relativistic positron gyro radius is according to:

$$R_L = \frac{1}{\omega_c}\left(1 - \frac{m_{positron}^2 C^4}{(E + m_{positron}C^2)^2}\right)^{1/2},$$

where

C is the speed of light;

E is the kinetic energy of the plurality of positrons, and $\omega_c$ is the relativistic gyro frequency of the positron.

17. The method of claim 16, wherein the relativistic gyro frequency of the positron is based on:

$$\omega_c = \frac{eB_0}{\gamma m_{positron}},$$

where e is the elementary charge, and $\gamma$ is the Lorentz factor.

* * * * *